US012778393B2

(12) United States Patent
Viering et al.

(10) Patent No.: US 12,778,393 B2
(45) Date of Patent: Nov. 3, 2026

(54) SYSTEMS, DEVICES, AND METHODS FOR FIBER OPTICAL DATA TRANSMISSION IN MEDICAL DEVICES

(71) Applicant: Boston Scientific Scimed, Inc., Maple Grove, MN (US)

(72) Inventors: Kirsten Viering, Newton, MA (US); Louis J. Barbato, Franklin, MA (US); Eric F. Brown, Wilmington, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 146 days.

(21) Appl. No.: 18/883,307

(22) Filed: Sep. 12, 2024

(65) Prior Publication Data

US 2025/0089998 A1 Mar. 20, 2025

Related U.S. Application Data

(60) Provisional application No. 63/582,939, filed on Sep. 15, 2023.

(51) Int. Cl.

| | |
|---|---|
| ***A61B 5/107*** | (2006.01) |
| ***A61B 1/00*** | (2006.01) |
| ***A61B 1/05*** | (2006.01) |
| ***A61B 1/06*** | (2006.01) |
| ***H04N 23/50*** | (2023.01) |

(52) U.S. Cl.

CPC ...... *A61B 1/00165* (2013.01); *A61B 1/00009* (2013.01); *A61B 1/05* (2013.01); *H04N 23/555* (2023.01); *A61B 1/00039* (2013.01); *A61B 1/00066* (2013.01)

(58) Field of Classification Search

CPC ... A61B 1/00165; A61B 1/00009; A61B 1/05; A61B 1/00039; A61B 1/00066; A61B 1/00013; A61B 1/045; A61B 1/00006; H04N 23/555

See application file for complete search history.

(56) References Cited

U.S. PATENT DOCUMENTS

2007/0232860 A1* 10/2007 Kubo ................. A61B 1/00096 600/160
2018/0332249 A1* 11/2018 Ogasawara ........ A61B 1/00006
2023/0200682 A1* 6/2023 Yoshioka ............. A61B 5/1076 600/593
2023/0371817 A1* 11/2023 Mizunaka .......... A61B 1/00006
2025/0089998 A1* 3/2025 Viering .............. A61B 1/00006

* cited by examiner

*Primary Examiner* — Howard D Brown, Jr.

(74) *Attorney, Agent, or Firm* — Bookoff McAndrews PLLC

(57) ABSTRACT

A medical device includes a shaft having a distal end and a proximal end, an image sensor at the distal end of the shaft, a distal conversion device at the distal end and in communication with the image sensor, a proximal photoreceiver, and an optical fiber extending between the distal conversion device and the proximal photoreceiver. The image sensor is configured to generate a first electrical signal based on a capture of one or more images, and the first electrical signal includes image or video data associated with the capture. The distal conversion device is configured to convert the first electrical signal to a light signal. The optical fiber is configured to facilitate transmission of the light signal between the distal conversion device and the proximal photoreceiver, and the proximal photoreceiver is configured to convert the light signal to a second electrical signal.

20 Claims, 9 Drawing Sheets

SYSTEMS, DEVICES, AND METHODS FOR FIBER OPTICAL DATA TRANSMISSION IN MEDICAL DEVICES

CROSS-REFERENCE TO RELATED APPLICATIONS

This application claims the benefit of priority under 35 U.S.C. § 119 from U.S. Provisional Application No. 63/582,939, filed Sep. 15, 2023, which is incorporated by reference herein in its entirety.

TECHNICAL FIELD

Various embodiments of this disclosure relate generally to systems, devices, and methods for fiber optical data transmission in medical devices. More particularly, various embodiments of this disclosure relate to systems, devices, and methods for using an optical fiber to transmit image and/or video data as a light signal from a distal end of medical devices to an image processing unit at a proximal end of the medical device.

BACKGROUND

Various medical devices include one or more image sensors at the distal end of the medical device, and the image sensor(s) may rely on copper wires for data transmission between the image sensor(s) and a video processor at a proximal end of the medical device. As such, the transmitted image and/or video data may be susceptible to disturbances due to electromagnetic interference (EMI). Alternatively or additionally, the transmitted image and/or video data may require careful design and/or planning to avoid unacceptable radiation from the medical device to other equipment in the vicinity, for example, for proper electromagnetic compatibility (EMC). EMI, as well as potential signal losses that may occur during video transmission, may lead to imaging artifacts and/or defects, such as noise, color shifts, or even loss of visualization.

Various aspects of this disclosure are directed to overcoming one or more of these above-referenced challenges.

SUMMARY OF THE DISCLOSURE

In some aspects, the techniques described herein relate to a medical device, including: a shaft having a distal end and a proximal end; an image sensor at the distal end of the shaft, wherein the image sensor is configured to generate a first electrical signal based on a capture of one or more images, the first electrical signal including image or video data associated with the capture of the one or more images; a distal conversion device at the distal end and in communication with the image sensor, wherein the distal conversion device is configured to convert the first electrical signal to a light signal; a proximal photoreceiver; and an optical fiber extending between the distal conversion device and the proximal photoreceiver, wherein the optical fiber is configured to facilitate transmission of the light signal between the distal conversion device and the proximal photoreceiver, wherein the proximal photoreceiver is configured to receive the light signal via the optical fiber and convert the light signal to a second electrical signal, the second electrical signal including a transmission of the image or video data associated with the capture of the one or more images.

In some aspects, the techniques described herein relate to a medical device, wherein the transmission of the image or video data includes a one-to-one transfer of the image or video data associated with the capture of the one or more images.

In some aspects, the techniques described herein relate to a medical device, further including: a handle connected to the proximal end of the shaft, wherein the handle includes an image processing unit communicatively coupled to the proximal photoreceiver.

In some aspects, the techniques described herein relate to a medical device, wherein the image processing unit is configured to process the second electrical signal to generate a video signal of the one or more images for a connectable display.

In some aspects, the techniques described herein relate to a medical device, wherein the image processing unit is further configured to: receive a user input or algorithmic input to adjust one or more settings for the image sensor; and generate a third electrical signal for the image sensor based on the user input or the algorithmic input.

In some aspects, the techniques described herein relate to a medical device, wherein the optical fiber is a first optical fiber, wherein the light signal is a first light signal, the medical device further including: a proximal conversion device in communication with the image processing unit; and a distal photoreceiver, wherein the proximal conversion device is configured to receive the third electrical signal and convert the third electrical signal to a second light signal; and a second optical fiber extending between the proximal conversion device and the distal photoreceiver, wherein the second optical fiber is configured to facilitate transmission of the second light signal between the proximal conversion device and the distal photoreceiver, wherein the distal photoreceiver is configured to receive the second light signal via the second optical fiber and convert the second light signal to a fourth electrical signal for transmission to the image sensor for adjusting the one or more settings.

In some aspects, the techniques described herein relate to a medical device, further including: a first lens positioned between the distal conversion device and the first optical fiber, wherein the first lens is configured to transmit the first light signal to the first optical fiber; and a second lens positioned between the proximal conversion device and the second optical fiber, wherein the second lens is configured to transmit the second light signal from the proximal conversion device to the second optical fiber.

In some aspects, the techniques described herein relate to a medical device, wherein the first lens is positioned proximal to the distal conversion device than to the first optical fiber, and wherein the second lens is positioned proximal to the proximal conversion device than to the second optical fiber.

In some aspects, the techniques described herein relate to a medical device, wherein the first lens and the second lens include at least one of: a ball lens, a gradient-index (GRIN) lens, or an aspheric lens.

In some aspects, the techniques described herein relate to a medical device, wherein the light signal is a first light signal, wherein the medical device is configured to receive the third electrical signal, the medical device further including: a distal beam splitter positioned to a distal end of the optical fiber; a proximal beam splitter positioned to a proximal end of the optical fiber; a distal photoreceiver positioned to the distal beam splitter; and a proximal conversion device positioned to the proximal beam splitter and in communication with the image processing unit, wherein the proximal conversion device is configured to convert the third electrical signal to a second light signal, wherein proximal beam splitter is configured to receive the second light signal and couple the second light signal to the optical fiber, wherein the distal beam splitter is configured to receive the second light signal via the optical fiber, and couple the second light signal to the distal photoreceiver, and wherein the distal photoreceiver is configured to convert the second light signal to a fourth electrical signal for processing by the image sensor for adjusting the one or more settings.

In some aspects, the techniques described herein relate to a medical device, wherein the distal conversion device includes a light illumination device.

In some aspects, the techniques described herein relate to a medical device wherein the first electrical signal includes an analog or a digital signal.

In some aspects, the techniques described herein relate to a medical device, wherein the first electrical signal is an analog electrical signal, wherein the light signal includes a plurality of pulsed light signals, and wherein converting the analog electrical signal to the plurality of pulsed light signals includes modulating the analog electrical signal based on a pulse width modulation (PWM) technique or a pulse position modulation (PPM) technique.

In some aspects, the techniques described herein relate to a medical device, wherein the first electrical signal is an analog electrical signal, wherein the light signal includes one or more on or off pulsed light signals, and wherein converting the analog electrical signal to the one or more on or off pulsed light signals includes modulating the analog electrical signal based on a pulse carrier technique or a pulse amplitude modulation (PAM) technique.

In some aspects, the techniques described herein relate to a medical device, wherein the first electrical signal is a digital electrical signal, and wherein converting the digital electrical signal to the light signal includes using a comparator circuit to determine whether the digital electrical signal is transmitting a binary one or a binary zero, wherein transmission of the binary one illuminates a light illumination device and transmission of the binary zero turns off the light illumination device, for generating the light signal.

In some aspects, the techniques described herein relate to a medical system, including: a medical device, including: a shaft having a distal end and a proximal end; an image sensor at the distal end of the shaft, wherein the image sensor is configured to generate a first electrical signal based on a capture of one or more images, the first electrical signal including image or video data associated with the capture of the one or more images; a distal conversion device at the distal end and in communication with the image sensor, wherein the distal conversion device is configured to convert the first electrical signal to a light signal; a proximal photoreceiver; an optical fiber extending between the distal conversion device and the proximal photoreceiver, wherein the optical fiber is configured to facilitate transmission of the light signal between the distal conversion device and the proximal photoreceiver; and an image processing unit, wherein the proximal photoreceiver is configured to receive the light signal via the optical fiber and convert the light signal to a second electrical signal, wherein the second electrical signal includes a transmission of the image or video data associated with the capture of the one or more images; and wherein the image processing unit is configured to process the second electrical signal to generate an image or video signal of the one or more images for a connectable display.

In some aspects, the techniques described herein relate to a medical system, wherein the image processing unit is located at a handle of the medical device.

In some aspects, the techniques described herein relate to a medical system, wherein the image processing unit is located separately from the medical device.

In some aspects, the techniques described herein relate to a medical system, including: a medical device, including: a shaft having a distal end and a proximal end; an image sensor at the distal end of the shaft, wherein the image sensor is configured to generate a first electrical signal based on a capture of one or more images, the first electrical signal including image or video data associated with the capture of the one or more images; a distal conversion device at the distal end and in communication with the image sensor, wherein the distal conversion device is configured to convert the first electrical signal to a light signal; a proximal photoreceiver; an optical fiber extending between the distal conversion device and the proximal photoreceiver, wherein the optical fiber is configured to facilitate transmission of the light signal between the distal conversion device and the proximal photoreceiver, wherein the proximal photoreceiver is configured to receive the light signal via the optical fiber and convert the light signal to a second electrical signal, wherein the second electrical signal includes a transmission of the image or video data associated with the capture of the one or more images; and an image processing unit configured to process the second electrical signal to generate a video signal of the one or more images for a connectable display, wherein the image processing unit is further configured to: receive a user input or algorithmic input to adjust one or more settings for the image sensor; and generate a third electrical signal for the image sensor based on the user input or the algorithmic input.

In some aspects, the techniques described herein relate to a medical system, wherein the optical fiber is a first optical fiber, wherein the light signal is a first light signal, and wherein the medical device is configured to receive the third electrical signal, the medical device further including: a proximal conversion device in communication with the image processing unit; a second optical fiber; and a distal photoreceiver, wherein the proximal conversion device is configured to receive the third electrical signal and convert the third electrical signal to a second light signal, wherein the second optical fiber extends between the proximal conversion device and the distal photoreceiver, wherein the second optical fiber is configured to facilitate transmission of the second light signal between the proximal conversion device and the distal photoreceiver, and wherein the distal photoreceiver is configured to receive the second light signal via the second optical fiber and convert the second light signal to a fourth electrical signal for transmission to the image sensor for adjusting the one or more settings.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DETAILED DESCRIPTION OF EMBODIMENTS

Figure 1:
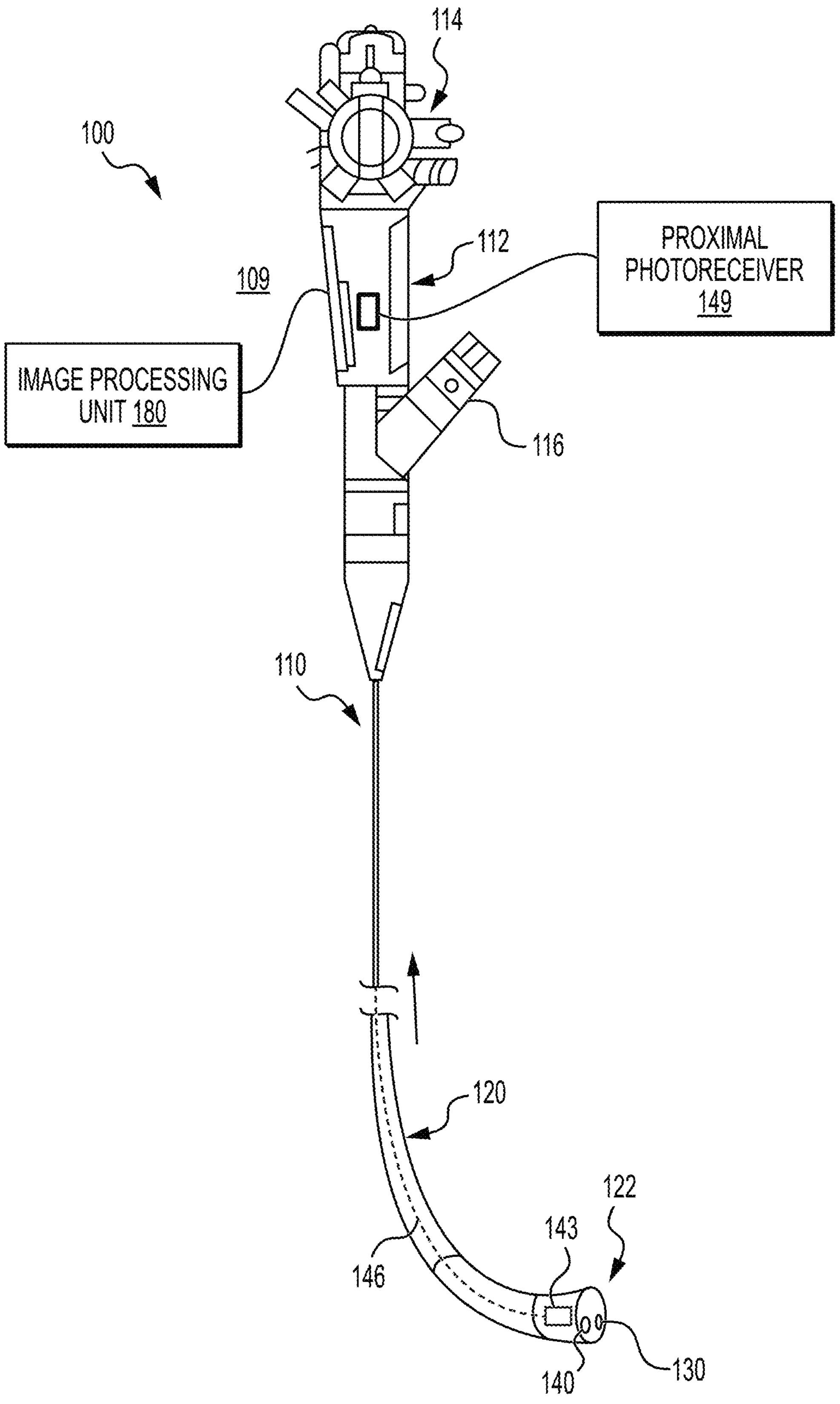
FIG. 1 depicts an exemplary medical system, according to one or more embodiments.

Both the foregoing general description and the following detailed description are exemplary and explanatory only and are not restrictive of the features, as claimed. As used herein, the terms "comprises," "comprising," "has," "having," "includes," "including," or other variations thereof, are intended to cover a non-exclusive inclusion such that a process, method, article, or apparatus that comprises a list of elements does not include only those elements, but may include other elements not expressly listed or inherent to such a process, method, article, or apparatus. In this disclosure, unless stated otherwise, relative terms, such as, for example, "about," "substantially," and "approximately" are used to indicate a possible variation of ±10% in the stated value. In this disclosure, unless stated otherwise, any numeric value may include a possible variation of ±10% in the stated value.

As described herein, the wireless communication protocols used for wireless communication between any two or more components may include one or more wireless communication protocols such as, for example, cellular, Wi-Fi®, Bluetooth®, Z-Wave®, ZigBee, near-field communication (NFC), or other wireless communication protocols.

Various embodiments of this disclosure relate generally to systems, devices, and methods for fiber optical data transmission in medical devices, and more particularly, to systems, devices, and methods for using an optical fiber to transmit image and/or video data as a light signal from a distal end of medical devices to an image processing unit at a proximal end of the medical device.

The terminology used below may be interpreted in its broadest reasonable manner, even though it is being used in conjunction with a detailed description of certain specific examples of the present disclosure. Indeed, certain terms may even be emphasized below; however, any terminology intended to be interpreted in any restricted manner will be overtly and specifically defined as such in this Detailed Description section.

As mentioned previously, some medical devices (e.g., video endoscopes or other medical devices with image or video capabilities) having one or more image sensors at a distal end of the medical device rely on copper wires for data transmission between the image sensor and a video processing unit. As such, the transmitted video data may require careful design and/or planning to avoid unacceptable radiation from the medical device to other equipment in the vicinity, for example, for proper electromagnetic compatibility (EMC). EMI, as well as potential signal losses that may occur during video transmission, may lead to imaging artifacts and/or defects, such as noise, color shifts, or even loss of visualization.

To remedy the issues described above, one or more embodiments describe a data transmission solution that does not rely on electronic or electrical signals for video data transmission, but rather uses photons in various ways to transmit video data in a medical device. As such, the video data being transmitted in a medical device may be less susceptible to EMI, and EMC may be less of a concern. To achieve this, one or more embodiments may include a medical device that includes an image sensor configured to generate an electrical signal based on a capture of one or more images. The electrical signal may be converted to a light signal by using a light emitting diode ("LED") or laser. The LED or laser may be coupled to one or more optical fibers for transmission through at least a portion of the length of the medical device. The optical fiber(s) may then be coupled to a photoreceiver at a proximal end of the medical device. The photoreceiver may be used to convert the light signal(s) from the optical fiber(s) back into an electrical format for processing by a video processing unit. The same optical fiber may be used to transmit light from the proximal end to the distal end of the medical device for power or other communication with the image sensor.

The above-mentioned embodiments may not need to use electrical conductor paths to support the image sensor(s) (e.g., camera) for operations such as illumination, clocking, and data transfer, among others, thereby helping to reduce disturbances and/or signal losses that may occur during transmission of video data. Further, the data generated by the image sensor(s) may be transmitted to the image processing unit with a one-to-one ratio.

Referring now to the drawings, FIG. 1 depicts an exemplary medical system 100, in accordance with one or more embodiments. The exemplary medical system 100 may include a medical device 110 and an image processing unit 180. In some aspects, the image processing unit 180 is separate from the medical device 110, and the medical device 110 and the image processing unit 180 may be communicatively coupled (e.g., wired or wireless) via an umbilicus 109. In other aspects, although not shown, the image processing unit 180 may be incorporated within one or more portions of the medical device 110. A general description for the distal components of the medical device 110 is provided first, followed by a general description of the image processing unit 180 below.

The medical device 110 may include any type of medical device, such as an endoscope, a duodenoscope, gastroscope, colonoscope, ureteroscope, bronchoscope, catheter, or other delivery or insertion system, and may include a handle 112, one or more actuation mechanisms 114, at least one port 116, and a shaft 120. The handle 112 of the medical device 110 may have one or more lumens (not shown) that communicate with a lumen(s) of one or more other components of the medical system 100. The handle 112 further includes the at least one port 116 that opens into the one or more lumens of the handle 112. As described in further detail herein, the at least one port 116 may be sized and shaped to receive one or more instruments therethrough, such as, for example, a catheter, a retrieval basket, an electrosurgical knife, a grasper, a stapler, etc., which may be used during a procedure. The shaft 120 may further include one or more lumens or working channels, which may terminate in one or more working channel openings 130 at a distal end of the shaft 120.

The medical device 110 is not drawn to any particular size or scale, and the shape and size of the medical device 110 described herein may vary as compared those shown. The medical device 110 is also not exhaustively illustrated in FIG. 1, and the medical device 110 may include other components although not shown. Alternatively, one or more of the components of the medical device 100 may be omitted in some cases.

An image sensor 140 may be located at a distal end of the shaft 120 near or on a distal tip 122. The image sensor 140 may be representative of one or more image sensors as can be appreciated. The image sensor 140 may include, for example, one or more color image sensors and/or monochromatic image sensors. The image sensor 140 may be configured to generate one or more analog signals and/or one or more digital signals, represented as one or more first electrical signals herein, carrying image and/or video data based on a capture of one or more images during a procedure (e.g., diagnostic procedure, pre-operation imaging, etc.). For example, the image sensor 140 may be configured and operable to capture a raw image (e.g., a digital and/or analog image) of a surrounding environment of the distal tip 122 of the shaft 120.

In some embodiments, the image sensor 140 may include a photosensor array (not shown) that may be configured and operable to convert a light beam received by the photosensor array into an electrical current. For example, the electrical current may be generated by the photosensor array arranged on the image sensor 140 when photons from the received light are absorbed by a plurality of photosites (not shown) arranged on the photosensor array. Further, each of the plurality of photosites may be operable to receive, capture, and absorb different wavelengths of the incoming light at a location of the photosites along a surface of the photosensor array. Accordingly, the plurality of photosites may capture the incoming light and may generate an electrical signal. The electrical signal may be is quantified and stored as a numerical value in a resulting processed image file. It should be appreciated that the photosensor array may include various suitable shapes, sizes, and/or configurations.

The image sensor 140 may be communicatively coupled (e.g., wired or wireless) to a distal conversion device 143 located at or near the distal end of the shaft 120. The distal conversion device 143 may include circuitry that may convert the one or more first electrical signals generated by the image sensor 140 into one or more first light signals (e.g., photons). The distal conversion device 143 may include one or more LEDs or lasers to generate the one or more first light signals.

The one or more LEDs or lasers may be communicatively coupled to a first optical fiber 146 to transmit the one or more first light signals through a length of the medical device 110, to a proximal photoreceiver 149, which may be located in or near the handle 112, among other locations. The proximal photoreceiver 149 may be coupled to a proximal end of the first optical fiber 146 to receive the one or more first light signals, and convert the one or more first light signals back into one or more second electrical signals for further processing by the image processing unit 180.

However, the location and placement of the proximal photoreceiver 149 is not limited thereto and may be changed depending on proximity to the image processing unit 180, location of a proximal end of the first optical fiber 146, among other factors. For example, in some aspects, the image processing unit 180 may be separate from the medical device 110, and the medical device 110 and the image processing unit 180 may be communicatively coupled via an umbilicus 109. In such a case, the proximal photoreceiver 149 may be located within the image processing unit 180, considering that the umbilicus 109 allows for transmission of light to the proximal photoreceiver 149. In other aspects, although not shown, the image processing unit 180 may be incorporated within one or more portions of the medical device 110.

The first optical fiber 146 may extend between the distal conversion device 143 and the proximal photoreceiver 149. The first optical fiber 146 may help to facilitate transmission of the one or more first light signals between the distal conversion device 143 and the proximal photoreceiver 149.

The image processing unit 180 may be a computer system incorporating a plurality of hardware components. The plurality of hardware components may help to allow the image processing unit 180 to receive data (e.g., image sensor data), process information (e.g., intensity, motion, spectral data, etc.), and/or generate a processed image or a video image stream for outputting to a user of the medical system 100 (e.g., via a user interface or other display).

The image processing unit 180 may include any computing device capable of executing machine-readable instructions, which may be stored on a non-transitory computer-readable medium, for example, of the image processing unit 180. Further, the image processing unit 180 may include a user interface operable to receive a user input thereon. The image processing unit 180 may be configured to process the one or more second electrical signals generated by the proximal photoreceiver 149 to generate one or more image and/or video signals of the images or video captured initially by the image sensor 140, for a connectable display. The connectable display may be a component of the image processing unit 180 or may be a separate display connected to the image processing unit 180 through wired or wireless connection.

In some embodiments, the medical system 100 is operable to accommodate and/or provide bidirectional communication between the image sensor 140 and the image processing unit 180, using the first optical fiber 146 or a second optical fiber. For example, bidirectional communication may be initiated when the image processing unit 180 receives a user input through a user interface to adjust one or more settings for the image sensor 140. Further description regarding this bidirectional communication is discussed below with respect to the later figures.

Although the image processing unit 180 is illustrated to be located in or near the handle 112, the image processing unit 180 may be located separately from the medical device 110. For example, the image processing unit 180 may be a separate computing device communicatively coupled to the medical device 110 via a wired or a wireless connection. As mentioned, the image processing unit 180 may be located in or near the handle 112, for example, by being operatively coupled to the handle 112 via the umbilicus 109. Further description regarding operation and arrangement of the image processing unit 140, the first optical fiber 146, the proximal photoreceiver 149, and the image processing unit 180 is discussed with respect to the later figures.

Figure 2:
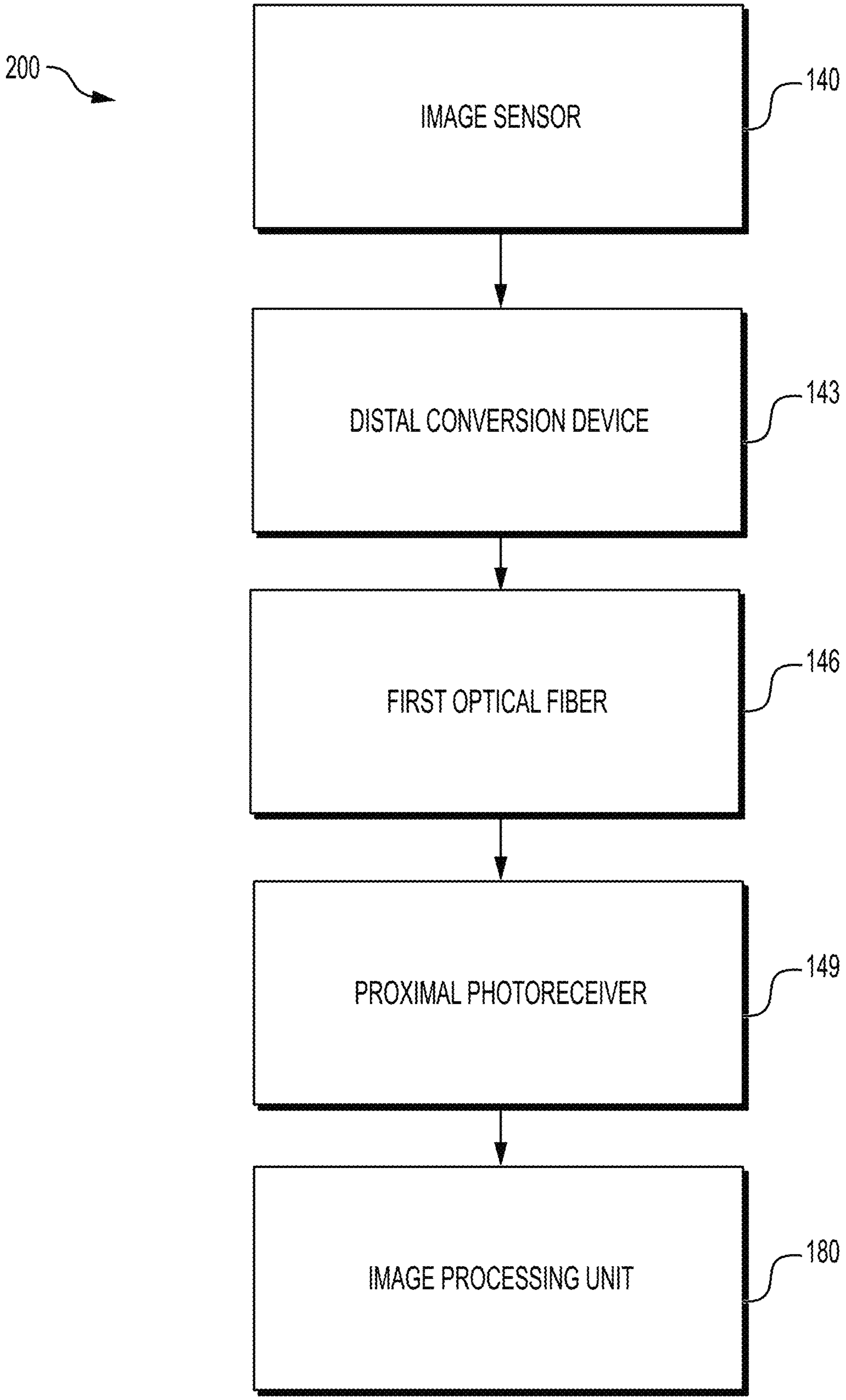
FIG. 2 depicts an exemplary upstream process for communication between an image sensor and an image processing unit for a medical device, according to one or more embodiments.

FIG. 2 depicts an exemplary upstream process 200 for communication between an image sensor 140 and an image processing unit 180 for a medical device, according to one or more embodiments. As way of example, the upstream process 200 may depict a flow of communication between an image sensor 140, a distal conversion device 143, a first optical fiber 146, a proximal photoreceiver 149, and an image processing unit 180 for a medical device, such as the medical device 110.

As mentioned, the image sensor 140 may be representative of one or more image sensors located at a distal end of the shaft 120 near or on the distal tip 122 of the medical device 110. The image sensor 140 may be configured to generate one or more analog signals and/or one or more digital signals, represented as one or more first electrical signals herein, carrying image and/or video data based on a capture of one or more images during a procedure (e.g., diagnostic procedure, pre-operation imaging, etc.). For example, the one or more image sensors may be configured and operable to capture a raw image (e.g., a digital and/or analog image) of a surrounding environment of the distal tip 122 of the shaft 120. The image sensor 140 may be communicatively coupled to the distal conversion device 143.

As mentioned, the distal conversion device 143 may be located at or near the distal end of the shaft 120. The distal conversion device 143 may include circuitry that may convert the one or more first electrical signals generated by the image sensor 140 into one or more first optical or light signals (e.g., photons). The distal conversion device 143 may further include one or more LEDs or lasers to generate the one or more first light signals. The one or more LEDs or lasers may be coupled to a first optical fiber 146 to transmit the one or more first light signals through a length of the medical device 110, to a proximal photoreceiver 149.

The first optical fiber 146 may extend between the distal conversion device 143 and the proximal photoreceiver 149, thereby facilitating transmission of the one or more first light signals between the distal conversion device 143 and the proximal photoreceiver 149. The first optical fiber 146 may extend from or near the distal end of the shaft 120 (e.g., coupled to the distal conversion device 103), and the first optical fiber 146 may be coupled to the proximal photoreceiver 149. The first optical fiber 146 may be used as a transmission medium for transferring the image and/or video data captured by the image sensor 140 to the image processing unit 180 in a way that mitigates signal loss, imaging artifacts and/or defects, and loss of visualization, among others.

The proximal photoreceiver 149 may be coupled to a proximal end of the first optical fiber 146 and may transmit data to the image processing unit 180. The proximal photoreceiver 149 may be located in or near the handle 112, among other locations. However, the location and placement of the proximal photoreceiver 149 is not limited thereto and may be changed depending on proximity to the image processing unit 180, location of a proximal end of the first optical fiber 146, among other factors. For example, in some aspects, the image processing unit 180 may be separate from the medical device 110, and the medical device 110 and the image processing unit 180 may be communicatively coupled via an umbilicus 109. In other aspects, although not shown, the image processing unit 180 may be incorporated within one or more portions of the medical device 110.

The proximal photoreceiver 149 may be configured to receive the one or more first light signals from the first optical fiber 146 and convert the one or more first light signals to one or more second electrical signals, for example, for processing by the image processing unit 180. The one or more second electrical signals may include a one-to-one transfer of the data included in the one or more first electrical signals generated by the image sensor 140.

The image processing unit 180 may be a computer system incorporating a plurality of hardware components. The plurality of hardware components may help to allow the image processing unit 180 to receive data (e.g., image sensor data), process information (e.g., intensity, motion, spectral data, etc.), and/or generate a processed image or a video image stream for outputting to a user of the medical system 100 (e.g., via a user interface or other display).

The image processing unit 180 may include any computing device capable of executing machine-readable instructions, which may be stored on a non-transitory computer-readable medium, for example, of the image processing unit 180. Further, the image processing unit 180 may include a user interface operable to receive a user input. The image processing unit 180 may be configured to process the one or more second electrical signals generated by the proximal photoreceiver 149 to generate one or more image or video signals of the images or video captured initially by the image sensor 140, for example, for a display. The display may be a component of the image processing unit 180 or may be a separate display connected to the image processing unit 180 through a wired or wireless connection.

Figure 3:
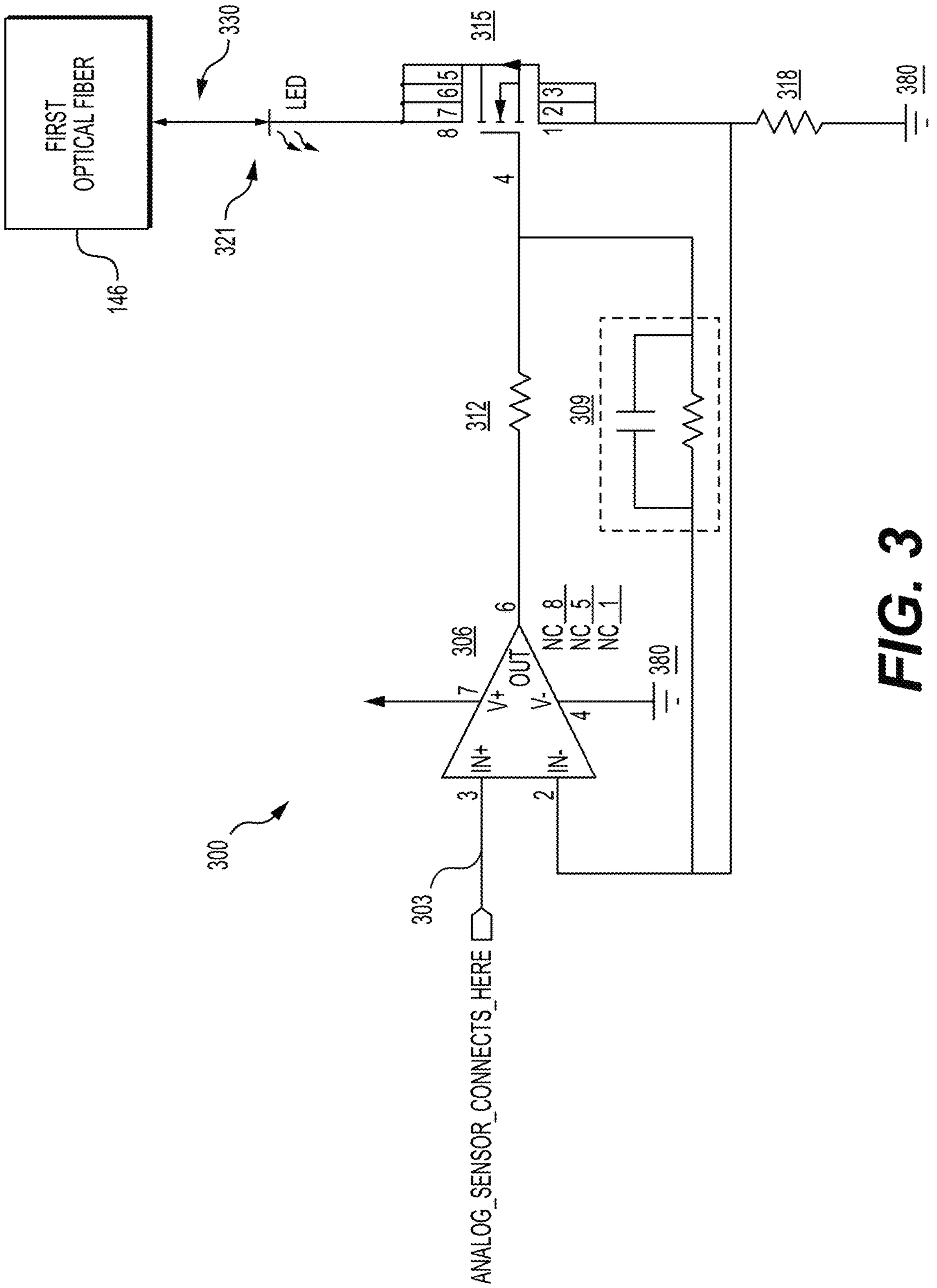
FIG. 3 depicts an exemplary circuit schematic that may be used for converting an analog signal to a light signal in a distal conversion device, according to one or more embodiments.

FIG. 3 depicts an exemplary circuit schematic 300 that may be used for converting an analog signal to a light signal in a distal conversion device, according to one or more embodiments. For example, the circuit schematic 300 may be used in the distal conversion device 143 for the medical device 110 for converting one or more first analog electrical signals to one or more first light signals at a distal end of the shaft 120. The circuit schematic 300 may include an amplifier 306, a first resistor 312, a parallel RC circuit 309, a semiconductor device 315, a second resistor 318, and a light source 321, among other components not specifically named. The light source 321 may include an LED, a laser, or one or more other light sources, as can be appreciated.

In the circuit schematic 300, an amplitude of one or more analog electrical signals 303 generated by the image sensor 140 (FIGS. 1 and 2) may be converted to one or more first light signals 330 (e.g., light intensity signal), which may be transmitted to the first optical fiber 146, as depicted. It is noted that the distal conversion device 143 is not limited to just the use of the circuit schematic 300. For example, the distal conversion device may convert one or more first analog electrical signals from the image sensor 140 to one or more first light signals for transmission via the first optical fiber 146 in one or more different ways than as described in association with the upstream process 200 in FIG. 2. The circuit schematic 300 is provided as an example only, and the distal conversion device 143 may be configured to use any circuitry suitable for converting analog electrical signals into light signals for conversion of the one or more analog electrical signals 303 into the one or more first light signals 330 as can be appreciated.

The one or more analog electrical signals 303 may be connected to a positive input (channel 3) of the amplifier 306. The second resistor 318 may be connected to a ground 380 and the semiconductor device 315. The second resistor 318 may be connected to a negative input (channel 2) of the amplifier 306 and the parallel RC circuit 309. The parallel RC circuit 309 may be connected to the negative input of the amplifier 306 and to the first resistor 312 and the semiconductor device 315. Negative supply V− of the amplifier 306 may be connected to the ground 380. Positive supply V+ of the amplifier 306 may be connected to a power source (not shown). The semiconductor device 315 may include a metal-oxide-semiconductor field-effect transistor (MOSFET) or other types of transistors.

In some cases, the one or more electrical signals 303 may be transmitted and/or converted using variable wavelengths of light. For example, a laser frequency of a light source (e.g., the light source 321) of the distal conversion device 143 may be shifted based on the amplitude of the one or more electrical signals 303. A spectrometer or interferometer at a proximal end of the first optical fiber 146 may be configured to decode the frequency shift back to an amplitude modulation of the one or more electrical signals 303.

Figure 4:
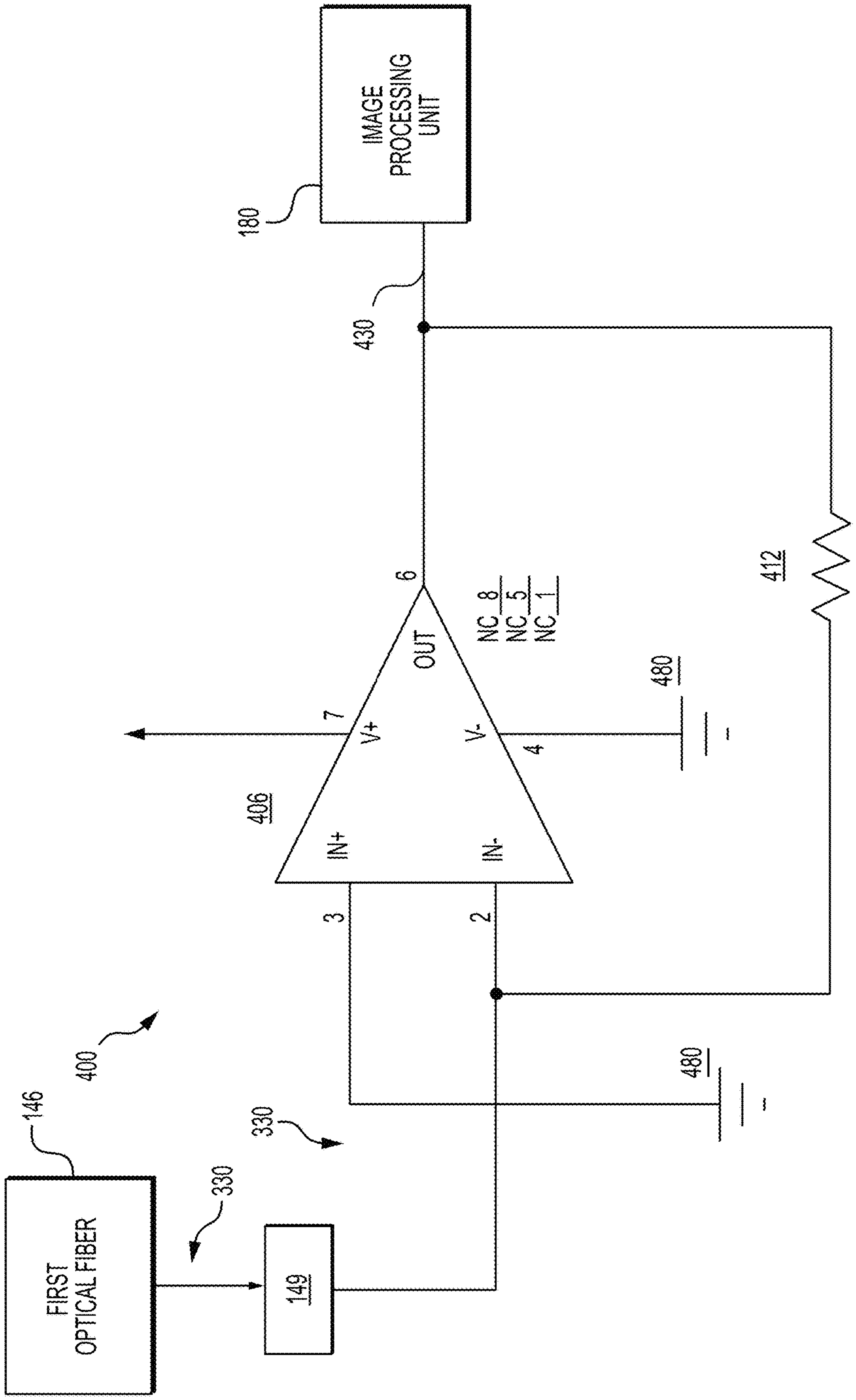
FIG. 4 depicts an exemplary circuit schematic that may be used for converting one or more light signals to one or more second electrical signals for a proximal photoreceiver, according to one or more embodiments.

FIG. 4 depicts an exemplary circuit schematic 400 that may be used for converting one or more light signals to one or more second electrical signals for a proximal photoreceiver, according to one or more embodiments. For example, the circuit schematic 400 may be used for the proximal photoreceiver 149 for the medical device 110 for converting one or more first light signals, such as the one or more first light signals 330, to one or more second electrical signals at or near a proximal end of the first optical fiber 146. The circuit schematic 400 may include an amplifier 406 and a first resistor 412, among other components not specifically named.

The one or more first light signals 330 may be transmitted to the proximal photoreceiver 149. The proximal photoreceiver 149 may be connected to a negative input (channel 2) of the amplifier 406 and the first resistor 412. Positive input (channel 3) and negative supply (V−) of the amplifier 406 may be connected to ground 480. Positive supply (V+) of the amplifier may be connected to a power source (not shown).

In the circuit schematic 400, the one or more first light signals 330, for example, may be converted to one or more second electrical signals 430, using the amplifier 406 as depicted. The one or more second electrical signals 430 may include analog and/or digital signals. The one or more second electrical signals 430 may be transmitted to the image processing unit 180 for further processing. It is noted that the proximal photoreceiver 149 is not limited to just the use of the circuit schematic 400 in converting one or more first light signals 330 from the first optical fiber 146 to one or more second electrical signals 430, for example, for processing by the image processing unit 180, as further described in association with the upstream process 200 in FIG. 2. The circuit schematic 400 is provided as an example only, and the proximal photoreceiver 149 may be configured to use any circuitry suitable for converting light signals into electrical signals as can be appreciated.

Figure 5:
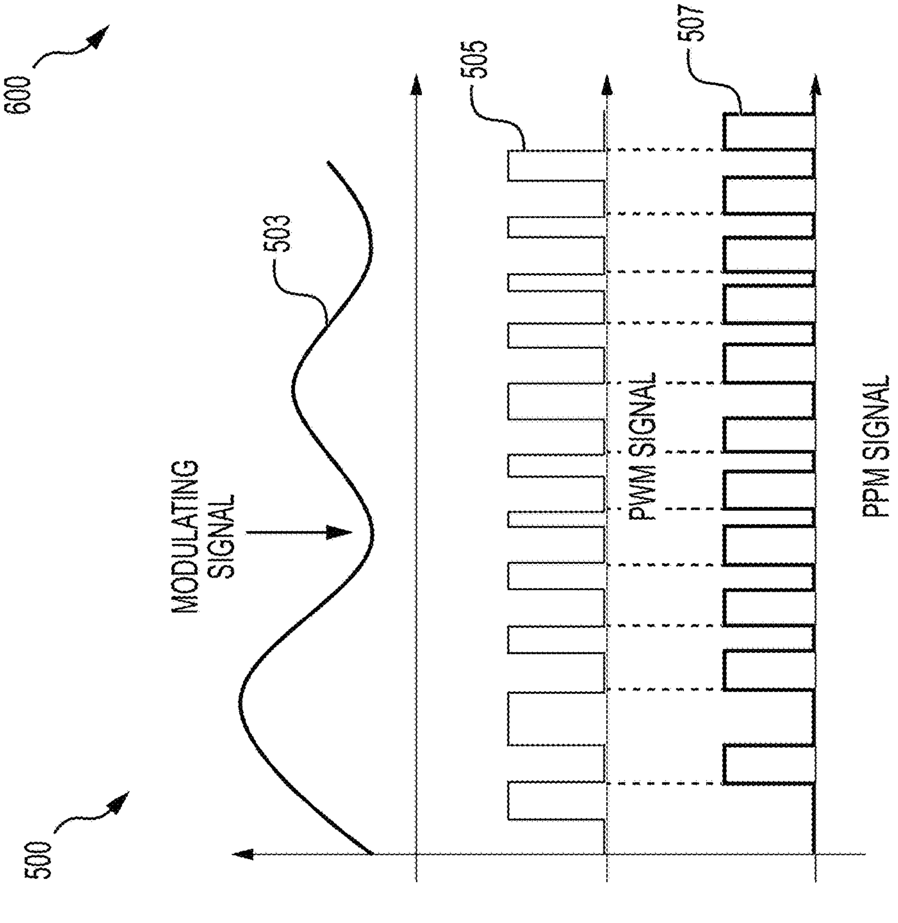
FIG. 5 depicts exemplary waveforms for modulating an analog signal output based on a pulse width modulation (PWM) method and/or a pulse position modulation method (PPM), according to one or more embodiments.

FIG. 5 depicts exemplary waveforms 500 for modulating an analog signal output based on a pulse width modulation (PWM) technique and/or a pulse position modulation technique (PPM), according to one or more embodiments. To better define a complete range (e.g., max amplitude) of an analog signal (e.g., corresponding to the one or more electrical signals 303) relative to the one or more first light signals (e.g., corresponding to the one or more first light signals 330), part to part variation may warrant individual calibration. The calibration may be performed at an end of the manufacturing line. Alternatively or additionally, the calibration may be performed where the values (e.g., light signals) are dark or low. Further, in some aspects, the calibration may be performed when the light signals corresponding to a fully saturated image sensor are measured and/or stored on or with a specific medical device 110.

Additionally and/or alternatively, one or more first electrical signals (e.g., the one or more electrical signals 303) generated by the image sensor 140 may be modulated based on a PWM and/or a PPM technique. In these aspects, the one or more first light signals generated by the distal conversion device 143 may include pulses of light of varying pulse widths, positions, and/or frequency. For example, analog signal waveform 503, which may correspond to the one or more analog electrical signals 303, may be modulated based on a PWM and/or a PPM technique to generate a PWM signal 505 and/or a PPM signal 507. The PWM signal 505 and the PPM signal 507 may include pulses of light of light of varying pulse widths, positions, and/or frequency. The one or more first light signals 330 may include the PWM signal 505 and/or the PPM signal 507.

Figure 6:
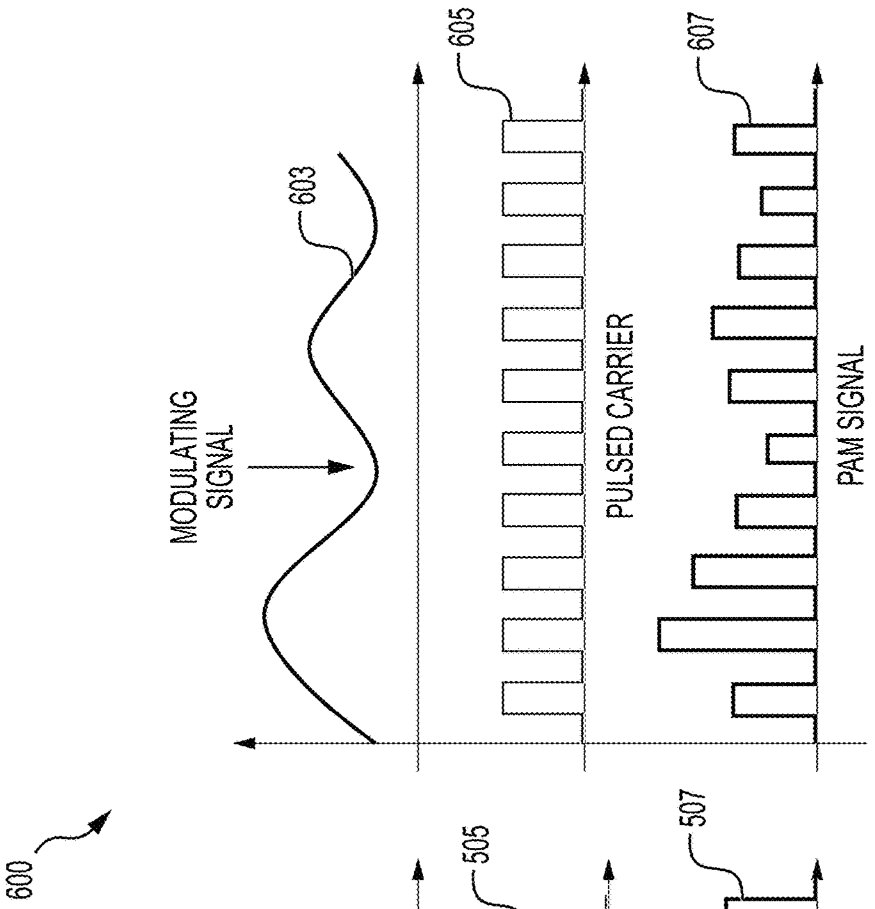
FIG. 6 depicts exemplary waveforms for modulating an analog signal output based on a pulse amplitude modulation (PAM) technique and/or a pulse carrier modulation technique, according to one or more embodiments.

FIG. 6 depicts exemplary waveforms 600 for modulating an analog signal output based on a pulse amplitude modulation (PAM) technique and/or a pulse carrier modulation technique, according to one or more embodiments. One or more first electrical signals (e.g., the one or more electrical signals 303) generated by the image sensor 140 may be modulated based on a PAM and/or a pulse carrier modulation technique. In these aspects, the one or more first light signals generated by the distal conversion device 143 may include one or more on or off pulsed light signals of varying amplitudes. For example, analog signal waveform 603, which may correspond to the one or more analog electrical signals 303, may be modulated based on a PAM and/or a pulse carrier modulation technique to generate a pulsed carrier signal 605 and/or a PAM signal 607. The pulsed carrier signal 605 and/or the PAM signal 607 may include one or more on or off pulsed light signals of varying amplitudes. The one or more first light signals 330 may include the pulsed carrier signal 605 and/or the PAM signal 607.

Figure 7:
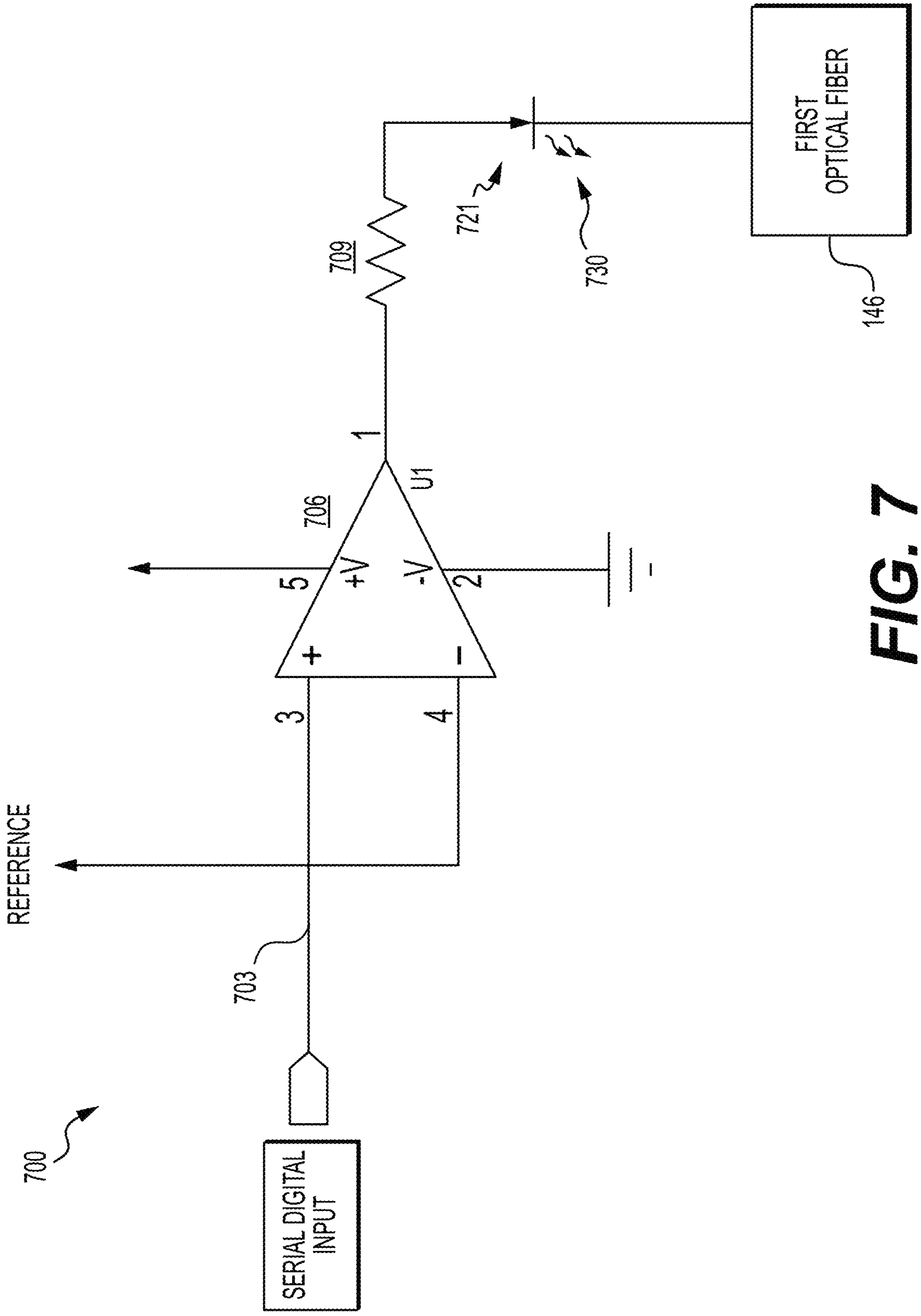
FIG. 7 depicts an exemplary circuit schematic that may be used for converting a digital signal to a light signal in a distal conversion device, according to one or more embodiments.

FIG. 7 depicts an exemplary circuit schematic 700 that may be used for converting a digital signal into a light signal in a distal conversion device, according to one or more embodiments. For example, the circuit schematic 700 may be used in the distal conversion device 143 for the medical device 110 for converting one or more first digital electrical signals to one or more first light signals at a distal end of the shaft 120. The circuit schematic 700 may include a comparator 706, a first resistor 709, and a light source 721, among other components not specifically named. The light source 721 may include an LED, a laser, or one or more other light sources, as can be appreciated.

In the circuit schematic 700, one or more digital electrical signals 703 generated by the image sensor 140 may be converted to one or more first light signals 730 as depicted. Information of the bits (high/low) of the one or more first digital electrical signals 703 may be used to generate "on" light signals or "off" light signals of the one or more first light signals 730, respectively. The comparator 706 may be used to determine when the serial digital input signal (e.g., the one or more digital electrical signals 703) is transmitting a binary "one" or a "zero." A transmitted binary "one" may put the digital signal above the reference voltage causing the output of the comparator 706 to output a voltage sufficient to illuminate the light source 721, while a transmitted binary "zero" may turn the light source 721 off. At the light source 721, a received "zero" may correspond to a ground reference or another reference level that may be selected or determined by a user or algorithm. In these aspects, when receiving a binary "one", the light source 721 may generate the one or more first light signals 730. The one or more first light signals 730 may be transmitted via the first optical fiber 146 as described in association with the upstream process 200 in FIG. 2.

The circuit schematic 700 is provided as an example only, and the distal conversion device 143 may be configured to use any circuitry suitable for converting digital electrical signals into light signals for conversion of the one or more digital electrical signals 703 into the one or more first light signals 730 as can be appreciated.

Figure 8:
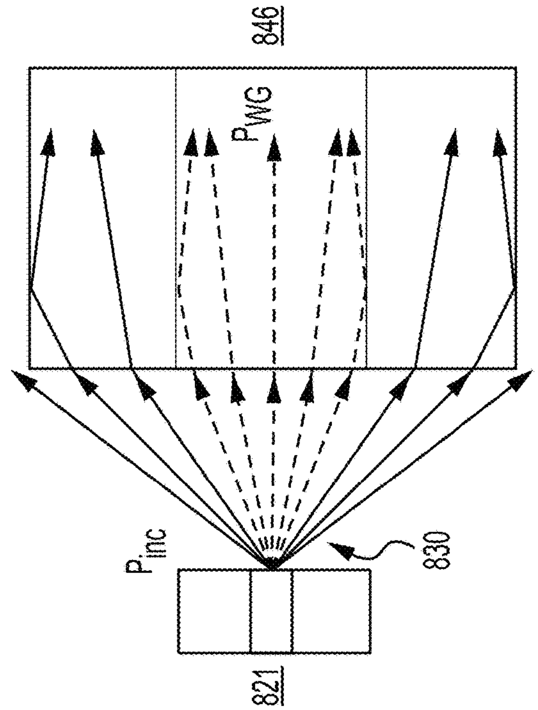
FIGS. 8-13 depict various coupling lenses or other coupling elements or methods that may be used to couple one or more light signals to an optical fiber, according to one or more embodiments.

FIGS. 8-13 depict use of various lenses (e.g., coupling lenses) or other methods that may be used to transmit one or more light signals to an optical fiber, according to one or more embodiments. In FIG. 8, a light source 821 may be configured to generate one or more light signals 830 for transmission into an optical fiber 846 without the use of a lens. The light source 821 may be similar to or interchangeable with the light source 321 and the light source 721 depicted in FIGS. 3 and 7, respectively, and may be used with the distal conversion device 143. For example, the light source 821 may be configured to generate the one or more light signals 830 based on one or more electrical signals (e.g., the one or more analog electrical signals 303 and/or the one or more digital electrical signals 703) generated by the image sensor 140. The light source 821 may include a LED configured to generate the one or more light signals 830. The one or more light signals 830 may be at least partially transmitted into the optical fiber 846, which may support a waveguided mode, among other modes. The one or more light signals 830 may be directly transmitted to the optical fiber 846 depending on appropriate characteristics (e.g., diameter, length, multi-mode, wavelength range, polarization properties, etc.) of the optical fiber 846.

In the example shown, some portions of the one or more light signals 830 may not be transmitted into a central core the optical fiber 846 due to dispersion of light that may occur as the one or more light signals 830 exit the light source 821. For example, some portions of the light signal of the one or more light signals 830 may disperse into the core or the cladding of the optical fiber 846 or miss the optical fiber 846 altogether. This dispersion may lead to signal loss, increased noise, and/or increased image/video artifacts depending on length of the optical fiber 846 and other factors. For various embodiments of this disclosure, the length of the optical fiber 846 implemented in the medical device 110 may include relatively short lengths where dispersion of some portions of light signals would not cause problems to the image and/or video signal being transmitted.

In the description provided below, use of various lenses are described that may direct light more effectively into an optical fiber for signal transmission. Use of lenses may help to reduce loss of the light emitted by the light sources, increase signal strength, decrease noise, and/or decrease image/video artifacts, among other benefits.

Figure 9:
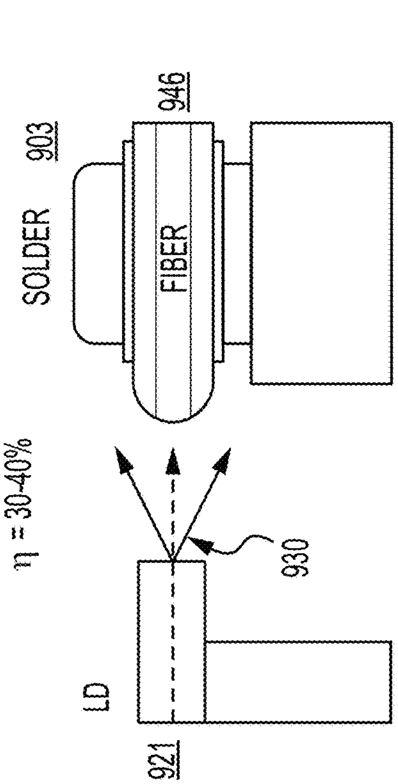

FIG. 9 depicts a light source 921 that may be configured to generate one or more light signals 930 for transmission into an optical fiber 946. The light source 921 may be similar to or interchangeable with the light source 321 and the light source 721 depicted in FIGS. 3 and 7, respectively, and may be used with the distal conversion device 143. For example, the light source 921 may include a laser configured to generate the one or more light signals 930 based on one or more electrical signals (e.g., the one or more analog electrical signals 303 and/or the one or more digital electrical signals 703) generated by the image sensor 140. The optical fiber 946 may further be bonded with a solder 903. The optical fiber 946 may support a waveguided mode, among other modes. The optical fiber 946 may be shaped to be curved, as depicted at a proximal end. The curved shape of the optical fiber 946 may allow more of the one or more light signals 930 to be directed into a central portion (e.g., core) of the optical fiber 946.

Figure 10:
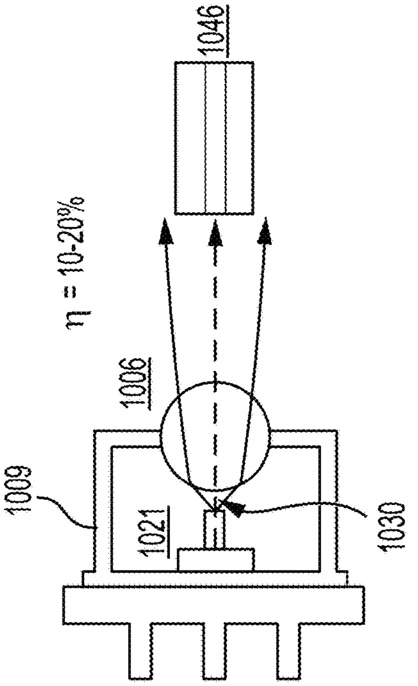

FIG. 10 depicts a light source 1021 that may be configured to generate one or more light signals 1030. The light source 1021 may be similar to or interchangeable with the light source 321 and the light source 721 depicted in FIGS. 3 and 7, respectively, and may be used with the distal conversion device 143. For example, the light source 1021 may be configured to generate the one or more light signals 1030 based on one or more electrical signals (e.g., the one or more analog electrical signals 303 and/or the one or more digital electrical signals 703) generated by the image sensor 140. A ball lens 1006 may be positioned in proximity to the light source 121 along a light path of the one or more light signals 1030. That is, the ball lens 1006 may be positioned between a proximal end of the light source 1021 and a distal end of the optical fiber 1046. In some aspects, the ball lens 1006 may be coupled to the light source 1021, for example, via one or more coupling arms 1009. Further, in some aspects, the ball lens 1006 may be positioned closer to the light source 1021 than to the optical fiber 1046. The ball lens 1006 may be used to help transmit the one or more light signals 1030 emitted by light source 1021 into the optical fiber 1046, as depicted. The ball lens 1006 may allow more of the one or more light signals 930 to be directed into a central portion (e.g., core) of the optical fiber 1046. The optical fiber 1046 may support a waveguided mode, among other modes.

Figure 11:
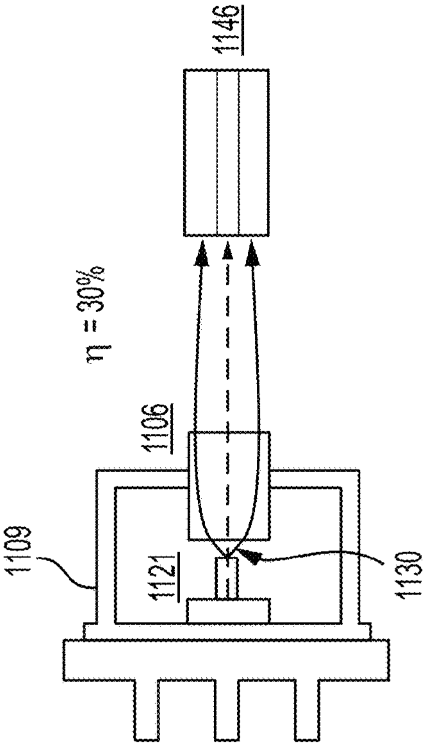

FIG. 11 depicts a light source 1121 that may be configured to generate one or more light signals 1130. The light source 1121 may be similar to or interchangeable with the light source 321 and the light source 721 depicted in FIGS. 3 and 7, respectively, and may be used with the distal conversion device 143. For example, the light source 1121 may be configured to generate the one or more light signals 1130 based on one or more electrical signals (e.g., the one or more analog electrical signals 303 and/or the one or more digital electrical signals 703) generated by the image sensor 140. A gradient-index (GRIN) lens 1106 may be positioned in proximity to the light source 1121 along a light path of the one or more light signals 1130. That is, the GRIN lens 1106 may be positioned between a proximal end of the light source 1121 and a distal end of the optical fiber 1146. In some aspects, the GRIN lens 1106 may be coupled to the light source 1121, for example, via one or more coupling arms 1109. Further, in some aspects, the GRIN lens 1106 may be positioned closer to the light source 1121 than to the optical fiber 1146. The GRIN lens 1106 may be used to help transmit the one or more light signals 1130 emitted by the light source 1121 to the optical fiber 1146, as depicted. The GRIN lens 1106 may enable more of the one or more light signals 1130 to be directed into a central portion (e.g., core) of the optical fiber 1146. The optical fiber 1146 may support a waveguided mode, among other modes.

Figure 12:
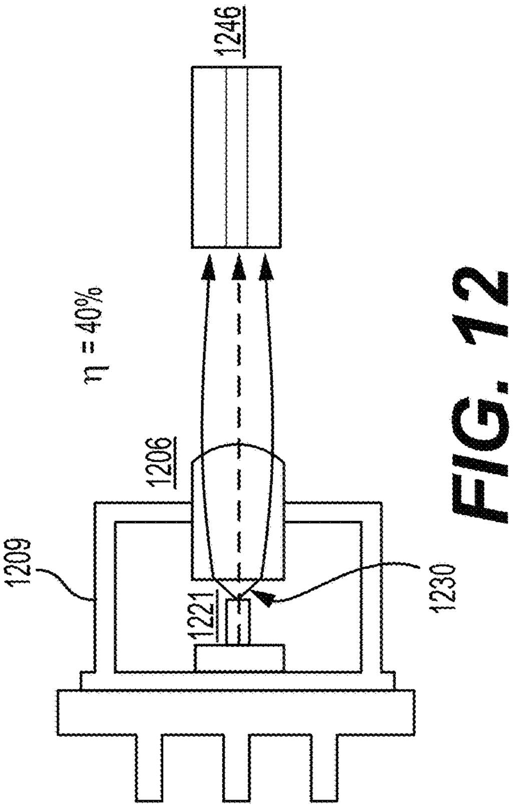

FIG. 12 depicts a light source 1221 that may be configured to generate one or more light signals 1230. The light source 1221 may be similar to or interchangeable with the light source 321 and the light source 721 depicted in FIGS.

3 and 7, respectively, and may be used with the distal conversion device 143. For example, the light source 1221 may be configured to generate the one or more light signals 1130 based on one or more electrical signals (e.g., the one or more analog electrical signals 303 and/or the one or more digital electrical signals 703) generated by the image sensor 140. An aspheric lens 1206 may be positioned in proximity to the light source 1121 along a light path of the one or more light signals 1230. That is, the aspheric lens 1206 may be positioned between a proximal end of the light source 1221 and a distal end of the optical fiber 1246. In some aspects, the aspheric lens 1206 may be coupled to the light source 1221, for example, via one or more coupling arms 1209. Further, in some aspects, the aspheric lens 1206 may be positioned closer to the light source 1221 than to the optical fiber 1246. The aspheric lens 1206 may be used to help transmit the one or more light signals 1230 emitted by the light source 1221 to the optical fiber 1246, as depicted. The aspheric lens 1206 may enable more of the one or more light signals 1230 to be directed into a central portion (e.g., core) of the optical fiber 1246. The optical fiber 1246 may support a waveguided mode, among other modes.

Figure 13:
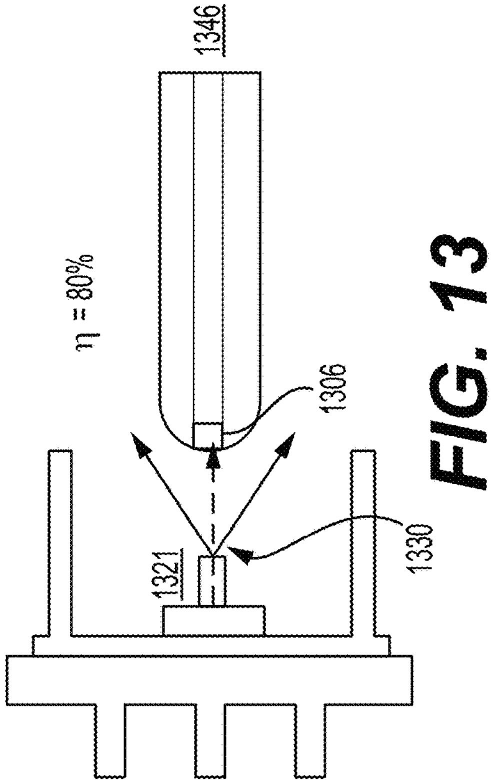

FIG. 13 depicts a light source 1321 that may be configured to generate one or more light signals 1330. The light source 1321 may be similar to or interchangeable with the light source 321 and the light source 721 depicted in FIGS. 3 and 7, respectively, and may be used with the distal conversion device 143. For example, the light source 1321 may be configured to generate the one or more light signals 1330 based on one or more electrical signals (e.g., the one or more analog electrical signals 303 and/or the one or more digital electrical signals 703) generated by the image sensor 140. A lens 1306 may be fused to a distal end of fiber 1346 as depicted. The lens 1306 may be used to help transmit the one or more light signals 1330 emitted by the light source 1321 to the optical fiber 1346 or to provide collimation into the optical fiber 136. The lens 1306 may enable more of the one or more light signals 1330 to be directed into a central portion (e.g., core) of the optical fiber 1346. The lens 1306 may include one or more shaped or GRIN lenses. The optical fiber 1346 may support a waveguided mode, among other modes.

Figure 14:
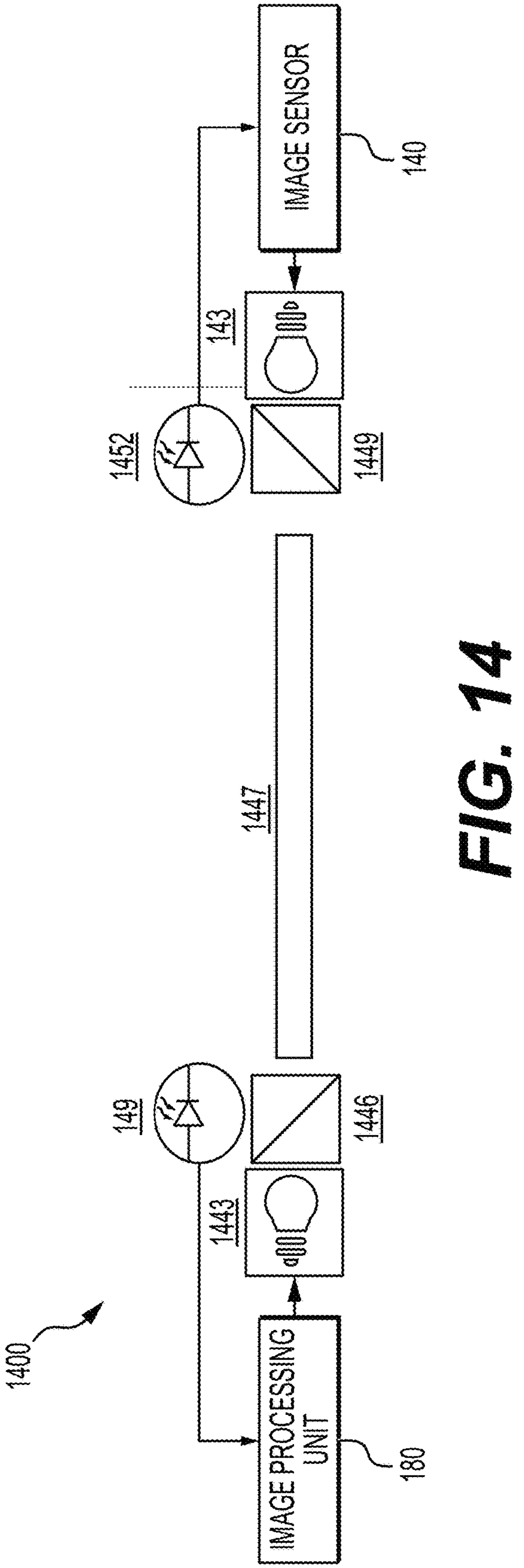
FIG. 14 depicts an exemplary schematic of two or more communication paths of a medical device incorporating beam splitters for bidirectional communication, according to one or more embodiments.

FIG. 14 depicts an exemplary schematic 1400 of two or more communication paths of the medical device 110 incorporating beam splitters, according to one or more embodiments. The schematic 1400 illustrates one or more bidirectional communication paths between the image processing unit 180 and the image sensor 140. For example, bidirectional communication may be initiated when the image processing unit 180 receives a user input through a user interface to adjust one or more settings for the image sensor 140. To enable the bidirectional communication, the medical device 110 may use a single optical fiber and a pair of beam splitters to direct the bidirectional communication between the image processing unit 180 and the image sensor 140.

The schematic 1400 includes a proximal conversion device 1443, a proximal beam splitter 1446, a proximal photoreceiver 149, a distal beam splitter 1449, a distal photoreceiver 1452, a distal conversion device 143, and an optical fiber 1447. The proximal conversion device 1443, the proximal beam splitter 1446, and the proximal photoreceiver 149 may be located in or near the handle 112 (FIG. 1). The proximal beam splitter 1446 may be positioned between the proximal conversion device 1443 and the optical fiber 1447. The proximal beam splitter 1446 may be coupled to a proximal end of the optical fiber 1447. Further, the proximal beam splitter 1446 may be coupled to the proximal conversion device 1443 and the proximal photoreceiver 149. However, the location of the proximal conversion device 1443, the proximal beam splitter 1446, and the proximal photoreceiver 149 may change depending on location of the image processing unit 180, location of a proximal end of the optical fiber 1447, among other factors.

The distal beam splitter 1449, the distal photoreceiver 1452, and the distal conversion device 143 may be located at or near the distal end of the shaft 120 (FIG. 1). The distal beam splitter 1449 may be positioned between the optical fiber 1447 and the distal conversion device 143. The distal beam splitter 1449 may be coupled to a distal end of the optical fiber 1447. Further, the distal beam splitter may be coupled to the distal photoreceiver 1452 and the distal conversion device 143. The optical fiber 1447 may extend between the proximal beam splitter 1446 and the distal beam splitter 1449. Further description regarding the location and function of the proximal components and distal components mentioned above, with respect to facilitating bidirectional communication between the image processing unit 180 and the image sensor 140, is provided below.

To initiate an upstream process of flow of communication from the image sensor 140 to the image processing unit 180 (e.g., similar to the upstream process 200 with respect to FIG. 2), the image sensor 140 may be configured to generate one or more analog signals and/or one or more digital signals, represented as one or more first electrical signals herein. The one or more first electrical signals convey image and/or video data based on a capture of one or more images (e.g., by the image sensor 140) during a procedure (e.g., diagnostic procedure, pre-operation imaging, etc.). The image sensor 140 may transmit the one or more first electrical signals to the distal conversion device 143. The distal conversion device 143 may be configured to convert the one or more first electrical signals into one or more first light signals and transmit the one or more first light signals to the distal beam splitter 1449.

The distal beam splitter 1449 may be configured to couple the one or more first light signals to the optical fiber 1447. For example, depending on the light source and the distal beam splitter 1449, the distal beam splitter 1449 may allow the one or more first light signals to be split into multiple paths, and direct a portion of the one or more first light signals into the optical fiber 1447 for transmission. In other cases, the distal beam splitter 1449 may not split the one or more first light signals into multiple paths and may transmit a majority of the one or more first light signals into the optical fiber 1447.

The proximal beam splitter 1446 (e.g., at a position proximal of a proximal end of the optical fiber 1447) may be configured to receive the one or more first light signals, or a portion of the one or more first light signals, via the optical fiber 1447. The proximal beam splitter 1446 may couple the one or more first light signals, or a portion of the one or more first light signals, to proximal photoreceiver 149. The proximal photoreceiver 149 may be configured to convert the one or more first light signals into one or more second electrical signals (e.g., analog and/or digital signal) for processing by the image processing unit 180. For example, the image processing unit 180 may receive and process the one or more second electrical signals to generate one or more image and/or video signals of the images and/or video originally captured by the image sensor 140, for a display.

To initiate a downstream process of flow of communication from the image processing unit 180 to the image sensor 140, the image processing unit 180 may receive a user input or determine an algorithmic input to adjust one or more settings for the image sensor 140 as described above. Based on the user input or the algorithmic input, the image processing unit 180 may generate one or more third electrical signals (e.g., analog and/or digital signals). The one or more third electrical signals include data associated with adjusting the one or more settings for the image sensor 140. The image processing unit 180 may be communicatively coupled to the proximal conversion device 1443 and transmit the one or more third electrical signals to the proximal conversion device 1443.

The proximal conversion device 1443 may include many of the same components as the distal conversion device 143, such as a light source. Additionally, the proximal conversion device 1443 may be configured to convert the one or more third electrical signals to one or more second light signals. To transmit the one or more second light signals via the optical fiber 1447, the proximal beam splitter 1446 may transmit the one or more second light signals, or a portion of the one or more second light signals, to the optical fiber 1447. For example, depending on the light source and the proximal beam splitter 1446, the proximal beam splitter 1446 may allow the one or more second light signals to be split into multiple paths, and direct a portion of the one or more second light signals into the optical fiber 1447 for transmission. In other cases, the proximal beam splitter 1446 may not split the one or more second light signals into multiple paths and may transmit a majority of the one or more second light signals into the optical fiber 1447.

The distal beam splitter 1449 (e.g., at a position distal to the distal end of the optical fiber 1447) may be configured to receive the one or more second light signals, or a portion of the one or more second light signals, via the optical fiber 1447. The distal beam splitter 1449 may transmit the one or more second light signals to the distal photoreceiver 1452. The distal photoreceiver 1452 may be configured to convert the one or more second light signals into one or more fourth electrical signals (e.g., analog and/or digital signal) for processing by the image sensor 140. For example, the image sensor 140 may receive and process the one or more fourth electrical signals to adjust the one or more settings specified by the user of the medical system 100.

For any of the upstream or downstream communication processes described above, a coupling lens (e.g., described with respect to FIGS. 9-13) may be positioned along a light transmission path between a light emitting source and an optical fiber. The coupling lens may allow a greater quantity of an emitted light signal to pass into the optical fiber. For example, a coupling lens may be positioned between the distal beam splitter 1449 and the optical fiber 1447. Additionally, a coupling lens may be positioned between the proximal beam splitter 1446 and the optical fiber 1447.

Figure 15:
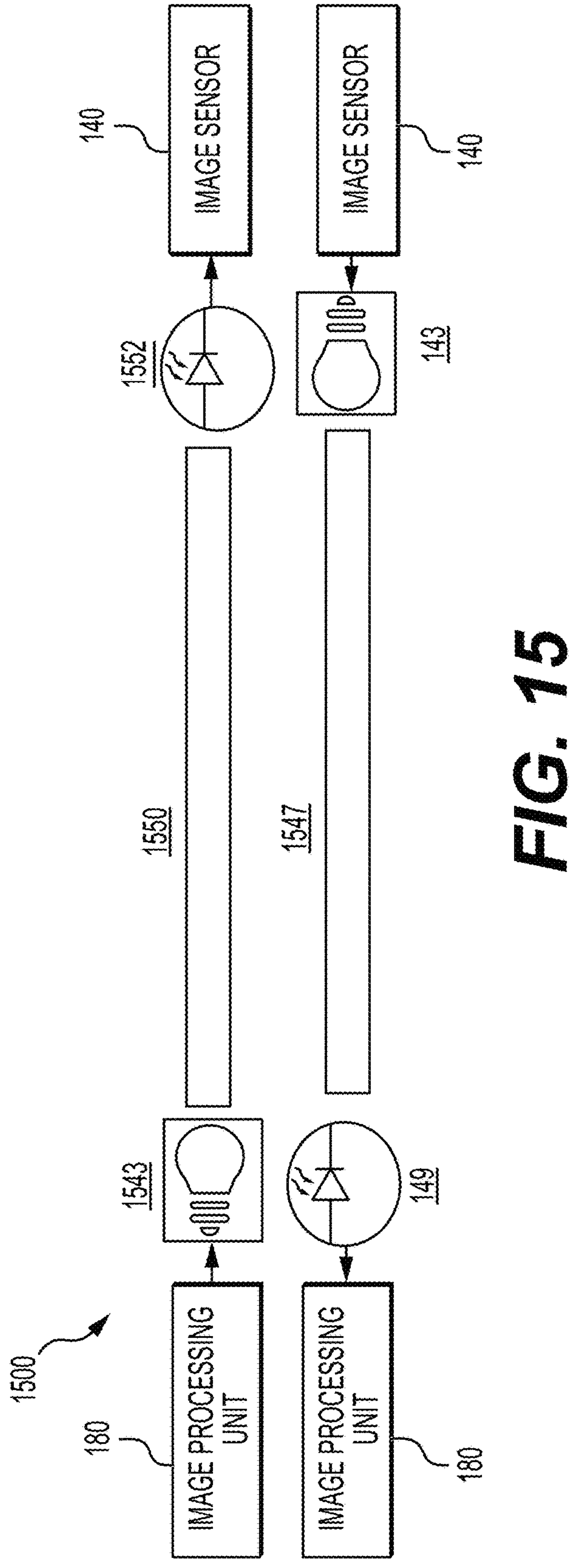
FIG. 15 depicts an exemplary schematic of two or more communication paths of a medical device incorporating a first optical fiber and a second optical fiber for bidirectional communication, according to one or more embodiments.

FIG. 15 depicts an exemplary schematic 1500 of two or more communication paths of the medical device 110 incorporating a first optical fiber and a second optical fiber, according to one or more embodiments. The schematic 1500 illustrates one or more bidirectional communication paths between the image processing unit 180 and the image sensor 140. For example, bidirectional communication may be initiated when the image processing unit 180 receives a user input through a user interface to adjust one or more settings for the image sensor 140. To enable the bidirectional communication, the medical device 110 may use a first optical fiber and a second optical fiber to direct the bidirectional communication between the image processing unit 180 and the image sensor 140.

The schematic 1500 includes a proximal conversion device 1543, a proximal photoreceiver 149, a distal photoreceiver 1552, a distal conversion device 143, a first optical fiber 1547, and a second optical fiber 1550. The proximal conversion device 1543 and the proximal photoreceiver 149 may be located in or near the handle 112. However, the location of the proximal conversion device 1543 and the proximal photoreceiver 149 may change depending on location of the image processing unit 180, among other factors.

The distal photoreceiver 1552 and the distal conversion device 143 may be located at or near the distal end of the shaft 120. The first optical fiber 1547 may extend between the proximal photoreceiver 149 and the distal conversion device 143. The second optical fiber 1550 may extend between the proximal conversion device 1543 and the distal photoreceiver 1552. Further description regarding the location and function of the proximal components and distal components mentioned above, with respect to facilitating bidirectional communication between the image processing unit 180 and the image sensor 140, is provided below.

To initiate an upstream process of flow of communication from the image sensor 140 to the image processing unit 180 (e.g., similar to the upstream process 200 with respect to FIG. 2), the image sensor 140 may be configured to generate one or more analog signals and/or one or more digital signals. The one or more analog signals and/or the one or more digital signals are represented as one or more first electrical signals herein. The one or more electrical signals may convey image and/or video data based on a capture of one or more images during a procedure (e.g., diagnostic procedure, pre-operation imaging, etc.). The image sensor 140 may transmit the one or more first electrical signals to the distal conversion device 143. The distal conversion device 143 may be configured to convert the one or more first electrical signals into one or more first light signals and transmit the one or more first light signals to the first optical fiber 1547.

The proximal photoreceiver 149 may be configured receive the one or more first light signals via the first optical fiber 1547 and convert the one or more first light signals into one or more second electrical signals (e.g., analog and/or digital signal) for processing by the image processing unit 180. For example, the image processing unit 180 may receive and process the one or more second electrical signals to generate one or more image and/or video signals of the images and/or video originally captured by the image sensor 140, for a connectable display.

To initiate a downstream process of flow of communication from the image processing unit 180 to the image sensor 140, the image processing unit 180 may receive a user input to adjust one or more settings for the image sensor 140 as described above. Based on the user input, the image processing unit 180 may generate one or more third electrical signals (e.g., analog and/or digital signals), which include data associated with adjusting the one or more settings for the image sensor 140. The image processing unit 180 may be communicatively coupled to the proximal conversion device 1543 and transmit the one or more third electrical signals to the proximal conversion device 1543.

The proximal conversion device 1543 may include many of the same components as the distal conversion device 143, such as a light source. Additionally, the proximal conversion device 1543 may be configured to convert the one or more third electrical signals to one or more second light signals. The proximal conversion device 1543 may be coupled to the second optical fiber 1550 and transmit the one or more second light signals to the second optical fiber 1550.

At the distal end of the second optical fiber 1550, the distal photoreceiver 1552 may be configured to receive the one or more second light signals via the second optical fiber 1550. The distal photoreceiver 1552 may be configured to convert the one or more second light signals into one or more fourth electrical signals (e.g., analog and/or digital signal) for processing by the image sensor 140. Similar to the proximal photoreceiver 149 (e.g., FIG. 4), the distal photoreceiver 1552 may be connected to various electronic devices and/or components (e.g., amplifier, attenuator, etc.), which may modulate the output signal levels to desired levels for processing by the image sensor 140. The image sensor 140 may receive and process the one or more fourth electrical signals to adjust the one or more settings specified by the user of the medical system 100.

For any of the upstream or downstream communication processes described above, a coupling lens (e.g., described with respect to FIGS. 8-13) may be positioned along a light transmission path between a light emitting source and an optical fiber. The coupling lens may allow a greater quantity of an emitted light signal to pass into the optical fiber. For example, a coupling lens may be positioned between the distal conversion device 143 and the first optical fiber 1547. Additionally, a coupling lens may be positioned between the proximal conversion device 1543 and the second optical fiber 1550.

With respect to the various embodiments described above, the image sensor 140 may be powered based on light sent by a light source (e.g., a laser) and transmitted through an optical fiber (e.g., optical fiber 1447, 1550, 1547, etc.). A distal photoreceiver (e.g., distal photoreceiver 1452, 1552, etc.) may convert the energy contained within the photons of the light signal into electrical energy, which may be used to power the image sensor 140.

The above-mentioned embodiments may not need to use electrical conductor paths to support the image sensor 140 (e.g., camera) for operations such as illumination, clocking, and data transfer, among others, thereby helping to reduce disturbances and/or signal losses that may occur during transmission of video and/or image data. Further, the data generated by the image sensor 140 may be transmitted to the image processing unit 180, and vice-versa, with a one-to-one ratio. Additionally, using one or more optical fibers may help to reduce the overall footprint of shaft 120, and/or help to increase the size of one or more working channels or lumens within shaft 120.

With respect to the schematic 1400 in FIG. 14, incorporation of the proximal beam splitter 1446 and the distal beam splitter 1449 to facilitate bidirectional communication may enable use of a single optical fiber (e.g., the optical fiber 1447). Using a single optical fiber may help to allow for the use of a shaft 120 of the medical device 110 with a smaller footprint (e.g., circumference, volume, etc.) as would otherwise be required for variations that may need more than one optical fiber. With respect to the schematic 1500 in FIG. 15, incorporation of the second optical fiber 1550 without using beam splitters may require a shaft 120 with a larger footprint; however, the footprint at the distal and proximal ends of the first optical fiber 1547 and the second optical fiber 1550 may be reduced.

Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A medical device, comprising:
- a shaft having a distal end and a proximal end;
- an image sensor at the distal end of the shaft, wherein the image sensor is configured to generate a first electrical signal based on a capture of one or more images, the first electrical signal including image or video data associated with the capture of the one or more images;
- a distal conversion device at the distal end and in communication with the image sensor,
  - wherein the distal conversion device includes an LED or a laser, and
  - wherein the distal conversion device is configured to convert the first electrical signal to a light signal, wherein the light signal transmits the image or video data;
- a proximal photoreceiver; and
- an optical fiber extending between the distal conversion device and the proximal photoreceiver,
- wherein the optical fiber is configured to facilitate transmission of the light signal between the distal conversion device and the proximal photoreceiver, and
- wherein the proximal photoreceiver is configured to receive the light signal via the optical fiber and convert the light signal to a second electrical signal, the second electrical signal including a transmission of the image or video data associated with the capture of the one or more images.

2. The medical device of claim 1, wherein the transmission of the image or video data includes a one-to-one transfer of the image or video data associated with the capture of the one or more images.

3. The medical device of claim 1, further comprising:
- a handle connected to the proximal end of the shaft, wherein the handle includes an image processing unit communicatively coupled to the proximal photoreceiver.

4. The medical device of claim 3, wherein the image processing unit is configured to process the second electrical signal to generate a video signal of the one or more images for a connectable display.

5. The medical device of claim 3, wherein the image processing unit is further configured to:
- receive a user input or algorithmic input to adjust one or more settings for the image sensor; and
- generate a third electrical signal for the image sensor based on the user input or the algorithmic input.

6. The medical device of claim 5, wherein the optical fiber is a first optical fiber, wherein the light signal is a first light signal, the medical device further comprising:
- a proximal conversion device in communication with the image processing unit; and
- a distal photoreceiver,
- wherein the proximal conversion device is configured to receive the third electrical signal and convert the third electrical signal to a second light signal; and
- a second optical fiber extending between the proximal conversion device and the distal photoreceiver, wherein the second optical fiber is configured to facilitate transmission of the second light signal between the proximal conversion device and the distal photoreceiver,
- wherein the distal photoreceiver is configured to receive the second light signal via the second optical fiber and convert the second light signal to a fourth electrical signal for transmission to the image sensor for adjusting the one or more settings.

7. The medical device of claim 6, further comprising:

a first lens positioned between the distal conversion device and the first optical fiber, wherein the first lens is configured to transmit the first light signal to the first optical fiber; and a second lens positioned between the proximal conversion device and the second optical fiber, wherein the second lens is configured to transmit the second light signal from the proximal conversion device to the second optical fiber.

8. The medical device of claim 7, wherein the first lens is positioned proximal to the distal conversion device than to the first optical fiber, and wherein the second lens is positioned proximal to the proximal conversion device than to the second optical fiber.

9. The medical device of claim 8, wherein the first lens and the second lens include at least one of: a ball lens, a gradient-index (GRIN) lens, or an aspheric lens.

10. The medical device of claim 6, wherein the light signal is a first light signal, wherein the medical device is configured to receive the third electrical signal, the medical device further comprising:

a distal beam splitter positioned to a distal end of the optical fiber;

a proximal beam splitter positioned to a proximal end of the optical fiber;

a distal photoreceiver positioned to the distal beam splitter; and a proximal conversion device positioned to the proximal beam splitter and in communication with the image processing unit, wherein the proximal conversion device is configured to convert the third electrical signal to a second light signal, wherein proximal beam splitter is configured to receive the second light signal and couple the second light signal to the optical fiber, wherein the distal beam splitter is configured to receive the second light signal via the optical fiber, and couple the second light signal to the distal photoreceiver, and wherein the distal photoreceiver is configured to convert the second light signal to a fourth electrical signal for processing by the image sensor for adjusting the one or more settings.

11. The medical device of claim 1, wherein the distal conversion device is coupled to the optical fiber.

12. The medical device of claim 1, wherein the first electrical signal includes an analog or a digital signal.

13. The medical device of claim 12, wherein the first electrical signal is an analog electrical signal, wherein the light signal includes a plurality of pulsed light signals, and wherein converting the analog electrical signal to the plurality of pulsed light signals includes modulating the analog electrical signal based on a pulse width modulation (PWM) technique or a pulse position modulation (PPM) technique.

14. The medical device of claim 12, wherein the first electrical signal is an analog electrical signal, wherein the light signal includes one or more on or off pulsed light signals, and wherein converting the analog electrical signal to the one or more on or off pulsed light signals includes modulating the analog electrical signal based on a pulse carrier technique or a pulse amplitude modulation (PAM) technique.

15. The medical device of claim 12, wherein the first electrical signal is a digital electrical signal, and wherein converting the digital electrical signal to the light signal includes using a comparator circuit to determine whether the digital electrical signal is transmitting a binary one or a binary zero, wherein transmission of the binary one illuminates a light illumination device and transmission of the binary zero turns off the light illumination device, for generating the light signal.

16. A medical system, comprising:

a medical device, comprising:

a shaft having a distal end and a proximal end;

an image sensor at the distal end of the shaft, wherein the image sensor is configured to generate a first electrical signal based on a capture of one or more images, the first electrical signal including image or video data associated with the capture of the one or more images;

a distal conversion device at the distal end and in communication with the image sensor, wherein the distal conversion device includes an LED or a laser, and wherein the distal conversion device is configured to convert the first electrical signal to a light signal, wherein the light signal transmits the image or video data;

a proximal photoreceiver;

an optical fiber extending between the distal conversion device and the proximal photoreceiver, wherein the optical fiber is configured to facilitate transmission of the light signal between the distal conversion device and the proximal photoreceiver; and an image processing unit, wherein the proximal photoreceiver is configured to receive the light signal via the optical fiber and convert the light signal to a second electrical signal, wherein the second electrical signal includes a transmission of the image or video data associated with the capture of the one or more images, and wherein the image processing unit is configured to process the second electrical signal to generate an image or video signal of the one or more images for a connectable display.

17. The medical system of claim 16, wherein the image processing unit is located at a handle of the medical device.

18. The medical system of claim 16, wherein the image processing unit is located separately from the medical device.

19. A medical system, comprising:

a medical device, comprising:

a shaft having a distal end and a proximal end;

an image sensor at the distal end of the shaft, wherein the image sensor is configured to generate a first electrical signal based on a capture of one or more images, the first electrical signal including image or video data associated with the capture of the one or more images;

a distal conversion device at the distal end and in communication with the image sensor, wherein the distal conversion device includes an LED or a laser, and wherein the distal conversion device is configured to convert the first electrical signal to a light signal, wherein the light signal transmits the image or video data;

a proximal photoreceiver;

an optical fiber extending between the distal conversion device and the proximal photoreceiver, wherein the optical fiber is configured to facilitate transmission of the light signal between the distal conversion device and the proximal photoreceiver, wherein the proximal photoreceiver is configured to receive the light signal via the optical fiber and convert the light signal to a second electrical signal, wherein the second electrical signal includes a transmission of the image or video data associated with the capture of the one or more images; and an image processing unit configured to process the second electrical signal to generate a video signal of the one or more images for a connectable display, wherein the image processing unit is further configured to:

receive a user input or algorithmic input to adjust one or more settings for the image sensor; and generate a third electrical signal for the image sensor based on the user input or the algorithmic input.

20. The medical system of claim 19, wherein the optical fiber is a first optical fiber, wherein the light signal is a first light signal, and wherein the medical device is configured to receive the third electrical signal, the medical device further comprising:

a proximal conversion device in communication with the image processing unit;

a second optical fiber; and a distal photoreceiver, wherein the proximal conversion device is configured to receive the third electrical signal and convert the third electrical signal to a second light signal, wherein the second optical fiber extends between the proximal conversion device and the distal photoreceiver, wherein the second optical fiber is configured to facilitate transmission of the second light signal between the proximal conversion device and the distal photoreceiver, and wherein the distal photoreceiver is configured to receive the second light signal via the second optical fiber and convert the second light signal to a fourth electrical signal for transmission to the image sensor for adjusting the one or more settings.

* * * * *